United States Patent
Takahashi (10) Patent No.: US 7,566,848 B2
(45) Date of Patent: Jul. 28, 2009

(54) CATALYTIC COMBUSTION TYPE GAS SENSOR

(75) Inventor: Ikuo Takahashi, Tokorozawa (JP)

(73) Assignee: Citizen Holdings Co., Ltd., Tokyo (JP)

( * ) Notice: Subject to any disclaimer, the term of this patent is extended or adjusted under 35 U.S.C. 154(b) by 526 days.

(21) Appl. No.: 11/444,413

(22) Filed: Jun. 1, 2006

(65) Prior Publication Data
US 2006/0289400 A1    Dec. 28, 2006

(30) Foreign Application Priority Data
Jun. 3, 2005    (JP) .............................. 2005-163877

(51) Int. Cl.
*H05B 1/02*    (2006.01)
(52) U.S. Cl. ....................... 219/494; 219/481; 219/497; 219/202; 374/102
(58) Field of Classification Search ................. 219/492, 219/481, 494.497, 499, 501, 505, 202–206; 374/101, 102, 120, 121
See application file for complete search history.

(56) References Cited
U.S. PATENT DOCUMENTS
6,921,883 B2 *  7/2005  Kato et al. .................. 219/494
7,193,187 B2 *  3/2007  Chen et al. .................. 219/490

FOREIGN PATENT DOCUMENTS
JP          3-162658 A       7/1991

* cited by examiner

*Primary Examiner*—Mark H Paschall
(74) *Attorney, Agent, or Firm*—Westerman, Hattori, Daniels & Adrian, LLP.

(57) ABSTRACT

A catalytic combustion type gas sensor includes a gas sensing unit 10, in which a sensing element having a heater coil embedded in a thermal conduction layer provided with an oxidation catalyst for causing a gas to be sensed to combust by contact, a compensation element having an equivalent heater coil embedded in a thermal conduction layer having no oxidation catalyst, and two resistor elements constitute a Wheatstone bridge circuit, outputs a voltage between the connection point of the sensing element and the compensation element and the connection point of the two resistor elements, as a detection signal, wherein a self-diagnosis unit is provided which diagnoses a sensor abnormality by comparing the slope of changes in voltage of the detection signal relative to changes in the voltage value of the direct-current voltage to be applied across the Wheatstone bridge circuit in an initial state and the slope of changes in voltage of the measurement value of the detection signal relative to changes in the voltage value of the direct-current voltage to be applied in a usage state.

9 Claims, 7 Drawing Sheets

CATALYTIC COMBUSTION TYPE GAS SENSOR

BACKGROUND OF THE INVENTION

1. Field of the Invention

The present invention relates to a catalytic combustion type gas sensor for sensing leakage of various kinds of gasses and, more particularly, to a catalytic combustion type gas sensor configured to be able to self-diagnose deterioration or operation abnormality due to use for a long time.

2. Description of the Related Art

Conventionally, a catalytic combustion type gas sensor has been known as a sensor for sensing combustible gasses such as a hydrogen gas, a methane gas, and so on. The catalytic combustion type gas sensor employs a sensing element, in which a heater coil is embedded in a thermal conduction layer (catalyst carrier) having an oxidation catalyst covering its surface or carrying the catalyst for causing a gas to be sensed to combust (oxidize) by contact, and energizes the heater coil of the sensing element to heat it to a predetermined temperature, so that when a combustible gas comes into contact with the oxidation catalyst and causes combustion, the combustion raises the temperature to change the resistance value of the heater coil. The sensor detects the change as a voltage to sense the presence of the combustible gas (see, for example, JP H3-162658A).

The above patent document also discloses a gas sensing apparatus configured such that, to compensate the effect by a change in ambient temperature, a compensation element is connected to the sensing element in series and connected in parallel with a series circuit in which two resistors are connected in series to constitute a Wheatstone bridge circuit, and a direct-current voltage is applied across the parallel circuit to detect the voltage between the connection point of the sensing element and the compensation element and the connection point of the two resistors. As the compensation element in this case, a compensation element is used which has a heater coil having the same electric property as that of the sensing element, embedded in a thermal conduction layer which is not covered with or does not hold the oxidation catalyst.

Such a catalytic combustion type gas sensor is widely used in various kinds of household and industrial equipment using a combustible gas and as a gas leakage sensing apparatus in a room having those kinds of equipment installed.

However, the catalytic combustion type gas sensor has a problem. The problem is that since the sensor is to be used for a long time, deterioration of the sensing element or the like and malfunction of circuits may occur, but such an abnormal state, if occurring, is not known because an actual gas leakage rarely occurs.

For this reason, conventionally, a gas to be sensed has been actually used to carry out an inspection of the sensing operation, or gas sensors in two lines have been provided for inspection and comparison or to increase safety.

However, periodical inspection using an actual gas takes a lot of trouble, and it is difficult, in particular, for an inspector to visit and inspect individually the gas sensor provided in a small-size household system. Another problem is that provision of the gas sensors in two lines leads to an increased cost, and therefore it is difficult to employ the gas sensors in two lines in the small-size system. Even if the gas sensors in two lines are provided, both of the sensors might possibly malfunction.

SUMMARY OF THE INVENTION

The present invention has been developed to solve the above-described problems, and its object is to configure a catalytic combustion type gas sensor such that when an abnormality such as deterioration or the like of the gas sensor occurs, the gas sensor can sense the abnormality by itself and inform of the abnormality even without inspection using an actual gas.

Figure 1:
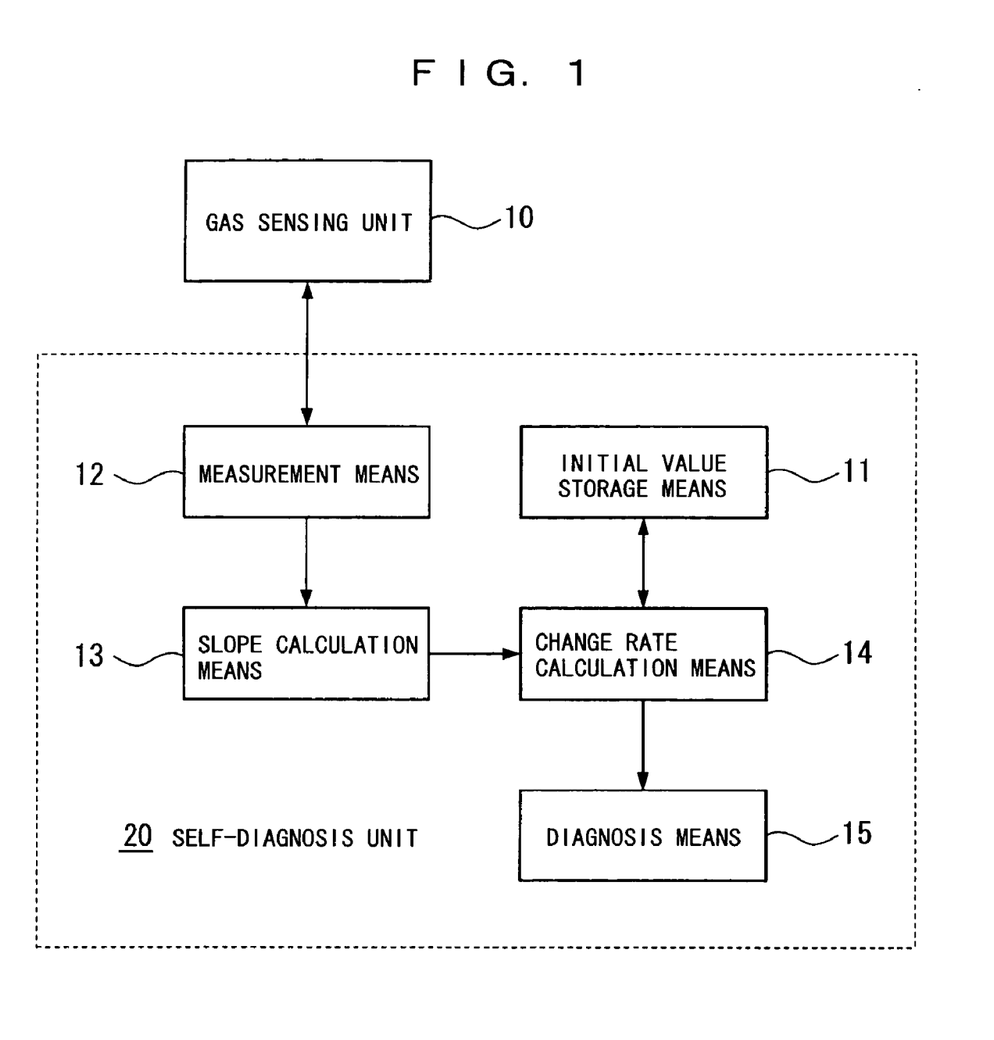
FIG. 1 is a functional block diagram showing a configuration of a basic embodiment of a catalytic combustion type gas sensor according to the invention.

The invention is, as shown in a functional block diagram in FIG. 1, a catalytic combustion type gas sensor including a gas sensing unit 10 having a first series circuit and a second series circuit connected in parallel to constitute a Wheatstone bridge circuit, the first series circuit having a sensing element and a compensation element connected in series, the sensing element having a heater coil embedded in a thermal conduction layer, the thermal conduction layer having an oxidation catalyst covering the surface thereof or carrying the catalyst, the oxidation catalyst causing a gas to be sensed to combust by contact, the compensation element having a heater coil with the same electric property as the heater coil of the sensing element embedded in a thermal conduction layer having no oxidation catalyst, and the second series circuit having a first resistor element and a second resistor element connected in series, in which a direct-current voltage is applied between connection points of the first series circuit and the second series circuit to output a voltage between a connection point of the sensing element and the compensation element and a connection point of the first resistor element and the second resistor element, as a detection signal, the gas sensor being characterized in that it includes a self-diagnosis unit 20 to attain the aforementioned object.

The self-diagnosis unit 20 has a function of diagnosing a sensor abnormality by comparing the slope of changes in voltage of the detection signal relative to changes in the voltage value of the direct-current voltage to be applied between the connection points in an initial state and the slope of changes in voltage of the measurement value of the detection signal relative to changes in the voltage value of the direct-current voltage to be applied between the connection points in a usage state.

It is preferable to configure the catalytic combustion type gas sensor such that the self-diagnosis unit has the following means of (a) to (e):

(a) an initial value storage means 11 for storing the changes in voltage or the slope of the voltage of the detection signal relative to the changes in the voltage value of the direct-current voltage to be applied between the connection points in the initial state;

(b) a measurement means 12 for measuring the changes in voltage of the detection signal relative to the changes in the voltage value of the direct-current voltage to be applied between the connection points in the usage state;

(c) a slope calculation means 13 for calculating, from the changes in voltage of the detection signal measured by the measurement means, the slope thereof;

(d) a change rate calculation means 14 for calculating the change rate of the slope from the slope calculated by the slope calculation means and an initial value of the slope stored in the initial value storage means or an initial value of the slope calculated from the stored changes in voltage of the detection signal; and (e) a diagnosis means 15 for diagnosing the sensor abnormality when the change rate of the slope calculated by the change rate calculation means exceeds a reference value.

Further, it is preferable to configure the above-described means in the catalytic combustion type gas sensor as follow:

The initial value storage means 11 is means for storing initial values of voltages of the detection signal when the direct-current voltage to be applied between the connection points in the initial state is switched among a rated voltage and voltages increased and decreased by predetermined percentages from the rated voltage, or of the slope of the zero points calculated from the voltages.

The measurement means 12 is means for automatically switching the direct-current voltage to be applied between the connection points to each voltage among the rated voltage and the voltages increased and decreased by the predetermined percentages from the rated voltage in the usage state to measure the voltages of the detection signal when the each voltage is applied.

The slope calculation means 13 is means for calculating the slope of the zero points from the voltage values measured by the measurement means 12.

The change rate calculation means 14 is means for calculating the change rate of the slope from the slope of the zero points calculated by the slope calculation means 13 and the initial value of the slope of the zero points stored in the initial value storage means 11 or the initial value of the slope of the zero points calculated from the stored voltages of the detection signal.

It is preferable that, in the catalytic combustion type gas sensor, the self-diagnosis unit 20 has a function of starting a self-diagnosis operation for a sensor abnormality in accordance with an instruction from equipment having the sensor attached thereto.

Alternatively, the self-diagnosis unit 20 may have a function of starting a self-diagnosis operation for a sensor abnormality periodically at preset time intervals.

Further, if the gas to be sensed is a hydrogen gas, the catalytic combustion type gas sensor is very effective as a gas sensor for sensing leakage of the hydrogen gas in a fuel cell system.

The catalytic combustion type gas sensor according to the invention can sense a malfunction such as deterioration or the like upon occurrence of it by the gas sensor itself without inspection using an actual gas and inform of the occurrence of malfunction, so that the gas sensor can increase the safety of a system or equipment using a combustible gas as well as eliminate an excessive cost required for check.

The above and other objects, features and advantages of the invention will be apparent from the following detailed description which is to be read in conjunction with the accompanying drawings.

DETAILED DESCRIPTION OF THE PREFERRED EMBODIMENTS

Hereinafter, a preferred embodiment for carrying out the invention will be concretely described with reference to the drawings.

Figure 2:
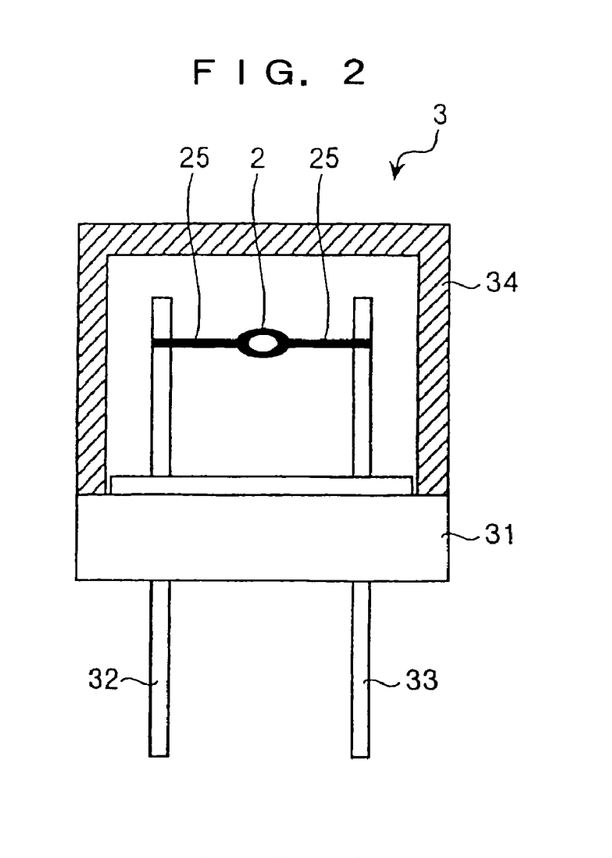
FIG. 2 is a partial cross-sectional view showing a configuration of a sensor main body to be used in one embodiment of the catalytic combustion type gas sensor according to the invention.

FIG. 2 is a partial cross-sectional view showing a configuration of a sensor main body to be used in one embodiment of a catalytic combustion type gas sensor according to the invention.

A sensor main body 3 has lead portions 25 on both sides of a sensing element 2 which are secured to electrode pins 32 and 33 for external connection penetrating a mount base 31 in a plate shape made of ceramic or resin. Further, a compensation element is provided side-by-side with the sensing element 2, though not shown in this drawing, which includes a heater coil having the same configuration and electric property as those of a heater coil of the sensing element 2. The sensing element 2 and the compensation element are surrounded by the mount base 31 and an explosion-proof structure 34 composed of a metal net having gas permeability or a sintered compact of metal powder or ceramic powder.

Figure 3:
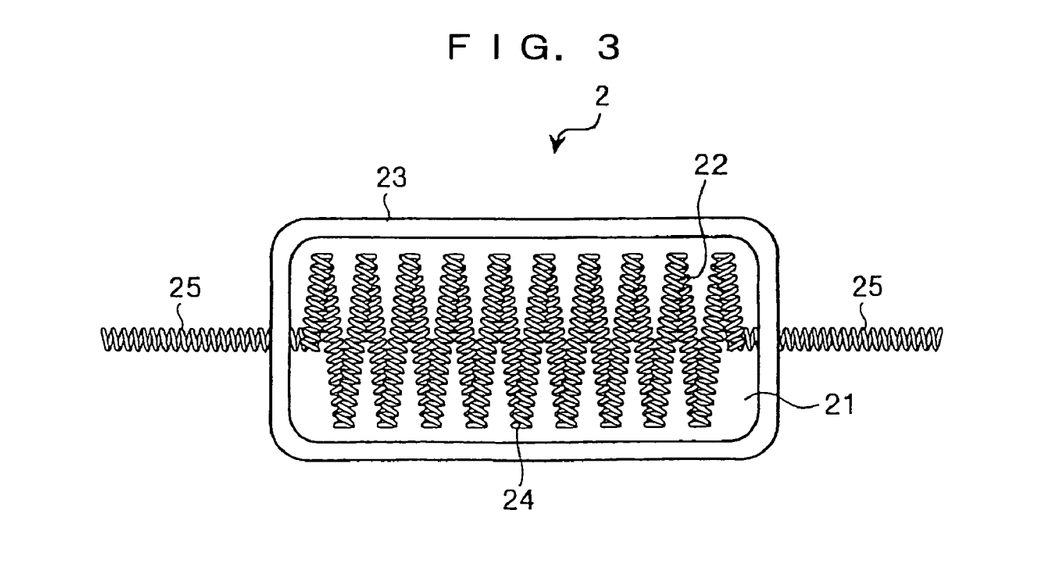
FIG. 3 is a cross-sectional view showing a configuration example of a sensing element in FIG. 2.

FIG. 3 is a cross-sectional view showing a configuration example of the sensing element 2. The sensing element 2 has a bead portion 24 of a heater coil 22 embedded in a thermal conduction layer 21 with an oxidation catalyst layer 23 covering the surface of the thermal conduction layer 21.

The heater coil 22 is made by winding a raw wire composed of a platinum wire or a platinum-based alloy wire made of a platinum-rhodium alloy or the like and having a wire diameter of about 10 μm to 50 μm, more preferably, about 20 μm to 30 μm, around a cored bar to form a single winding coil and then winding the single winding coil around the cored bar again into double windings to form a portion which is to be the bead portion 24. This structure increases the area where the heater coil 22 is in contact with the thermal conduction layer 21 and increases the resistance of the heater coil 22, thereby achieving a high gas sensitivity. The lead portion 25 is also composed of a single-winding coil and can absorb an impact from the outside, thus presenting a sensor resistant to the impact. The heater coil is, however, not limited to the above-described one, but may employ a conventional general heater coil which has a bead portion composed of a single-winding coil and a lead portion in a linear shape.

The thermal conduction layer 21 is made of, for example, alumina (aluminum oxide $Al_2O_3$). The thermal conduction layer of the not-shown compensation element is formed of the same material so as to have the same heat capacity. The oxidation catalyst layer 23 is made of metal oxide according to a combustible gas to be sensed. The oxidation catalyst layer 23 is then heated to a temperature according to the combustible gas to be sensed by application of a voltage between the both ends of the heater coil 22. In the case where the gas to be sensed is a methane gas, the oxidation catalyst layer 23 is heated to about 450° C. Note that the thermal conduction layer of the compensation element is not covered with the oxidation catalyst.

The oxidation catalyst layer 23 uses a catalyst causing the gas to be sensed to oxidize and combust by contact and made by dispersing, for example, platinum (Pt) and palladium (Pd) in tin oxide ($SnO_2$).

Examples of the gas to be sensed include, for example, a methane gas, a hydrogen gas, an LP gas (liquefied petroleum gas), a propane gas, a butane gas, an ethylene gas, a carbon monoxide gas, organic component gasses such as ethanol, acetone, and so on.

Figure 4:
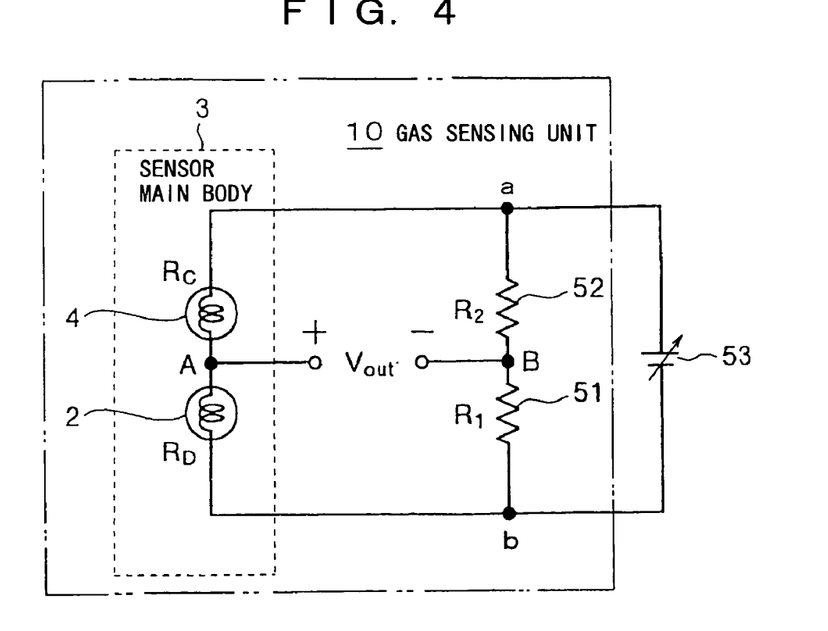
FIG. 4 is a circuit diagram of a Wheatstone bridge circuit being a gas sensing unit shown in FIG. 1 and a power supply for applying a direct-current voltage to the circuit.

FIG. 4 is a circuit diagram of a Wheatstone bridge circuit forming a gas sensing unit 10 shown in FIG. 1 and a power supply for applying a direct-current voltage to the circuit.

The gas sensing unit 10 has a first series circuit in which the sensing element (D element) 2 and the compensation element (C element) 4 of the sensor main body 3 are connected in series and a second series circuit in which a first resistor element 51 and a second resistor element 52 are connected in series, which circuits are connected in parallel to constitute the Wheatstone bridge circuit. A direct-current voltage is applied by a power supply 5 between connection points a-b of the first series circuit and the second series circuit to output, as a detection signal, a voltage Vout between a connection point A of the sensing element 2 and the compensation element 4 and a connection point B of the first resistor element 51 and the second resistor element 52.

The output voltage Vout of the Wheatstone bridge circuit is zero volt (0 mV) when $R_1 \times R_2 = R_D \times R_C$, where energizing resistance values of the sensing element 2, the compensation element 4, the first resistor element 51, and the second resistor element 52 are $R_D$, $R_C$, $R_1$, and $R_2$, respectively. Note that it is desirable to employ the first resistor element 51 and the second resistor element 52 having the same resistance value and temperature property.

When the power supply 5 which can vary the output voltage applies a rated voltage across the series circuit constituted of the heater coil 22 of the sensing element 2 and the heater coil of the compensation element 4, the sensing element 2 and the compensation element 4 become operation temperature, so that, in a clean atmosphere, the output voltage Vout is obtained which is dependent on the energizing resistance values $R_D$ and $R_C$ in a state where the heat supply component from the heater coils embedded in the elements and the heat release component diffused into the atmosphere are balanced. The output voltage at this time is called a "zero-point value." If the gas to be sensed exists and comes into contact with the oxidation catalyst layer 23 of the sensing element 2 to combust, the temperature of the heater coil 22 rises to increase only the energizing resistance value $R_D$, so that the output voltage Vout increases to the plus (+) side by an amount according to the gas sensitivity.

Figure 5:
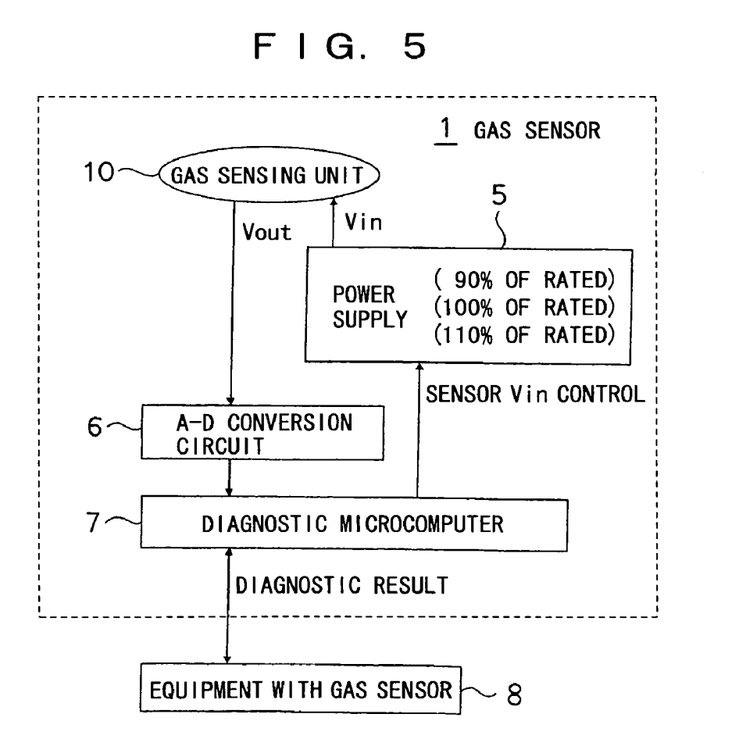
FIG. 5 is a block diagram showing a configuration of a concrete embodiment of the catalytic combustion type gas sensor according to the invention.
Figure 6:
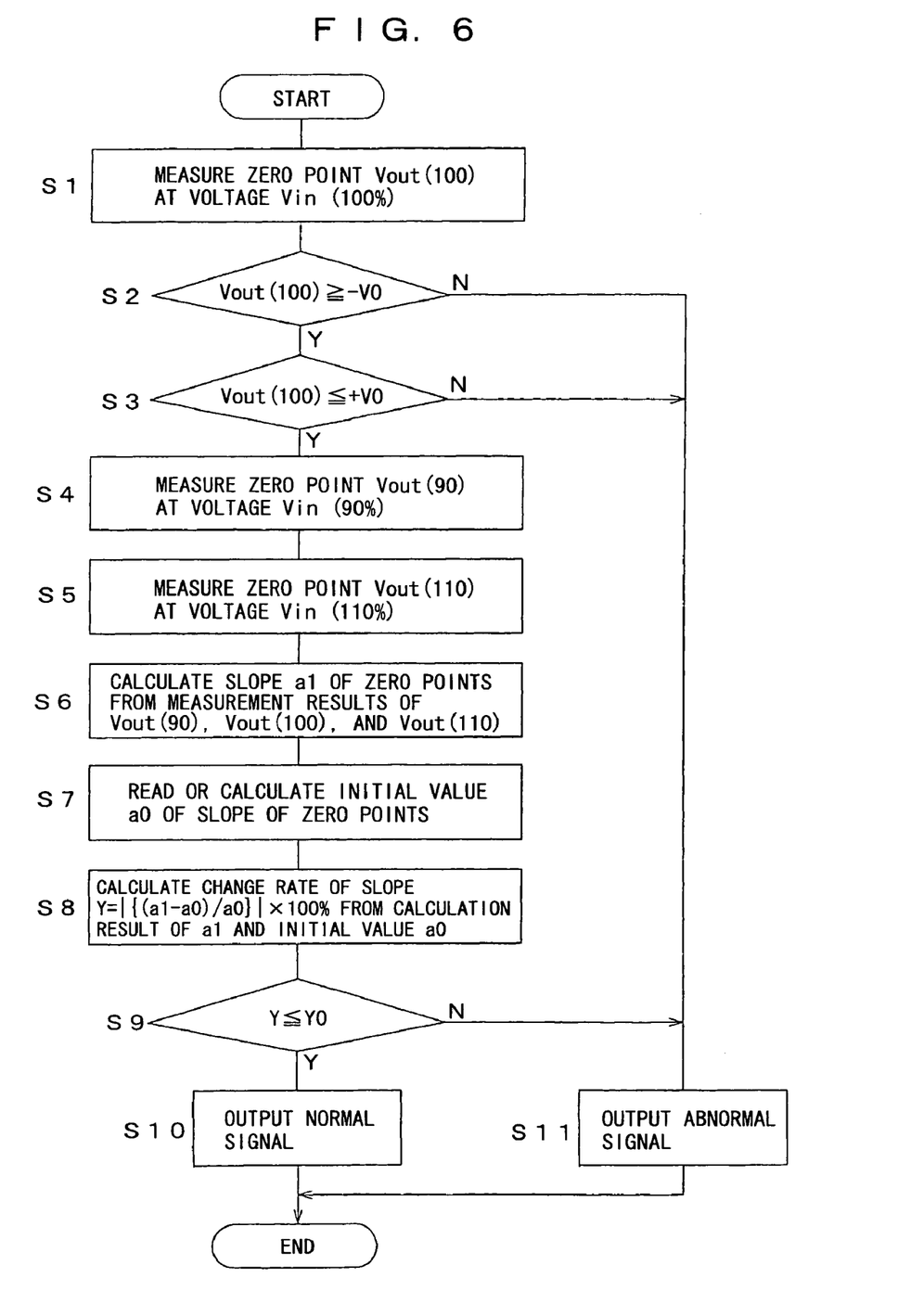
FIG. 6 is a flowchart showing contents of a self-diagnosis processing by a diagnostic microcomputer in FIG. 5.

FIG. 5 is a block diagram showing a configuration of a concrete embodiment of the catalytic combustion type gas sensor according to the invention. FIG. 6 is a flowchart showing contents of a self-diagnosis processing by a diagnostic microcomputer 7 of the catalytic combustion type gas sensor.

A gas sensor 1 shown in FIG. 5 is the catalytic combustion type gas sensor and composed of the gas sensing unit 10 shown in FIG. 4, the power supply 5, an A-D conversion circuit 6, and the diagnostic microcomputer 7.

The diagnostic microcomputer 7 is composed of, similarly to a general microcomputer, a CPU being a central processing unit, a ROM being a read only memory, a RAM being a writable and readable memory, a timer, and an I/O port and so on. The ROM stores a program for self-diagnosis processing shown in FIG. 6 and a later-described data of initial values as well as a program for gas sensing processing.

The diagnostic microcomputer 7, the power supply 5 which can vary a voltage Vin to be applied to the gas sensing unit 10 according to a control signal from the diagnostic microcomputer 7, and the A-D conversion circuit 6 which converts the output voltage from the gas sensing unit 10 into a digital signal and inputs the signal into the diagnostic microcomputer 7 serve as each means of a self-diagnosis unit 20 shown in FIG. 1. The self-diagnosis function will be described later.

Figure 7:
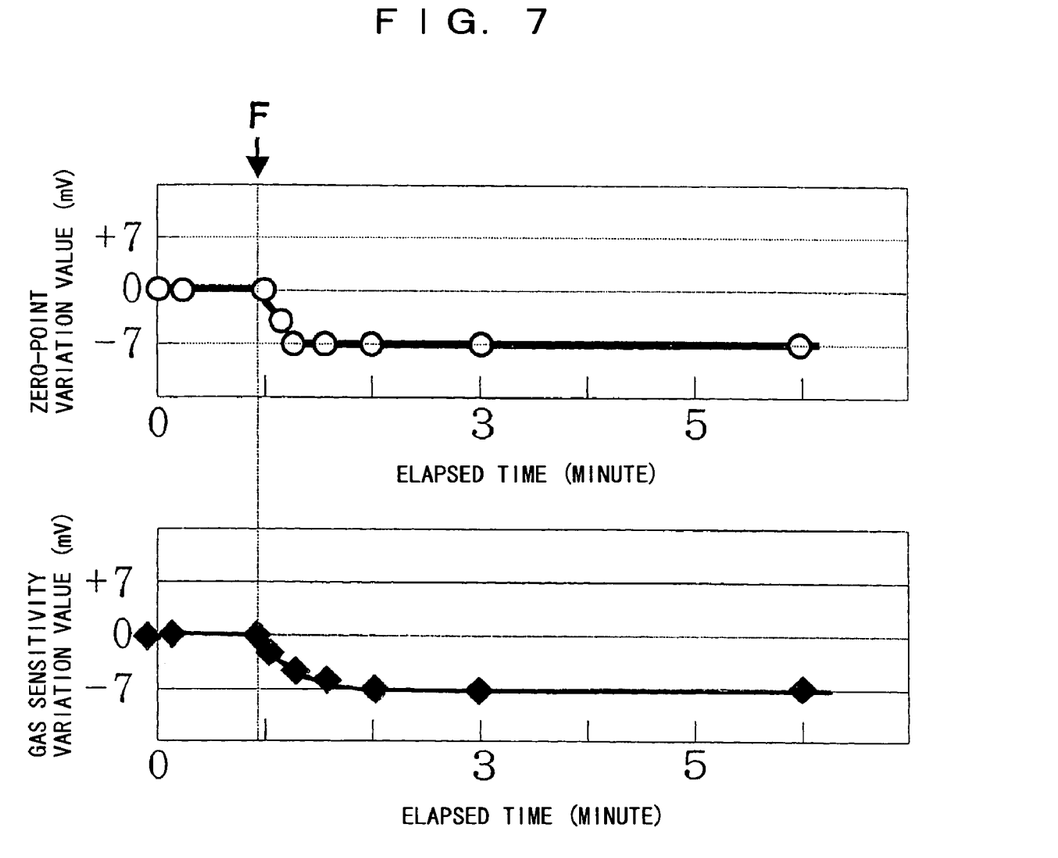
FIG. 7 is a diagram showing an example of the zero-point variation and the gas sensitivity variation when a cause of a poor condition is placed during operation of the catalytic combustion type gas sensor.

FIG. 7 shows the zero-point variation and the gas sensitivity variation (where methane gas, 4000 ppm is regarded as the gas to be sensed) as examples of output variation when a cause of a poor condition is placed at the point in time shown by an arrow F during operation of the catalytic combustion type gas sensor. The zero-point variation due to the poor condition is caused by variation in one or both of the energizing resistance value $R_D$ of the sensing element and the energizing resistance value $R_C$ of the compensation element, and can be relatively easily found by comparing the measurement value after variation to the initial value.

On the other hand, the gas sensitivity variation (deterioration) occurs when the value of increase in the energizing resistance value $R_D$ of the sensing element at the time of gas detection is smaller than the initial value. In most cases, the cause of the deterioration also induces a change in surface area of one or both of the sensing element and the compensation element.

As described above, the zero-point value of the gas sensor in the clean atmosphere is defined by the magnitude relation between the energizing resistance value $R_D$ of the sensing element and the energizing resistance value $R_C$ of the compensation element. One of the factors of the relation is the each surface area of both elements, so that the deterioration in gas sensitivity can be indirectly known when reviewing the change in the zero point corresponding to the change in the surface areas.

Hence, the supply voltage of the rated value and the voltage varied into voltages of 90% and 110% of the rated value were applied in sequence to the gas sensing unit of the sensor main body which was intentionally deteriorated in gas sensitivity, and the zero-point values being the output voltages in the clean atmosphere were measured and plotted, the tendencies as shown in FIG. 8 to FIG. 11 were obtained, leading to understanding that the deterioration in gas sensitivity can be grasped as a change in slope of the zero points with respect to the applied voltages.

Figure 8:
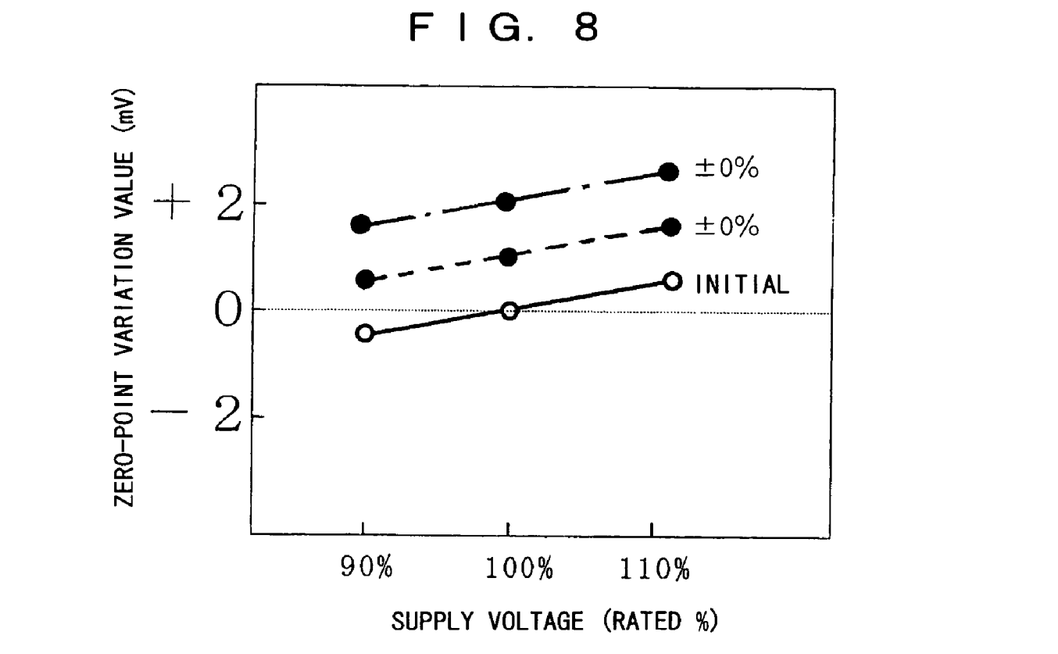
FIG. 8 is a diagram showing an example of the zero-point variation and the hydrogen sensitivity due to application of an impact to the sensor main body.
Figure 9:
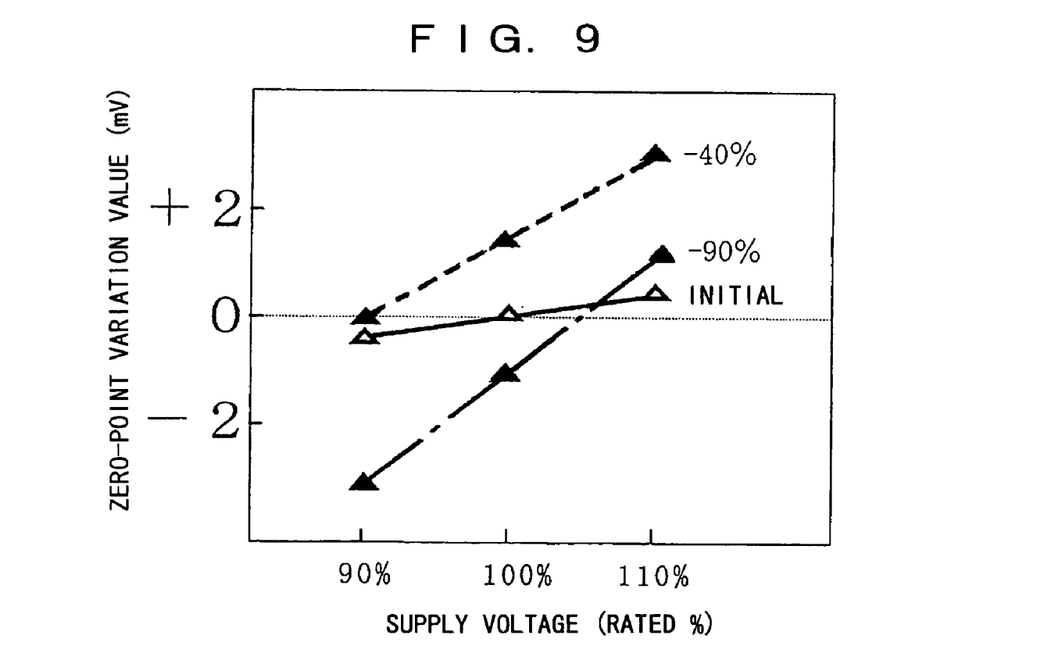
FIG. 9 is a diagram showing an example of the zero-point variation and deterioration in hydrogen sensitivity due to immersion of the sensor main body into 10% aqueous solution of sulfuric acid.
Figure 10:
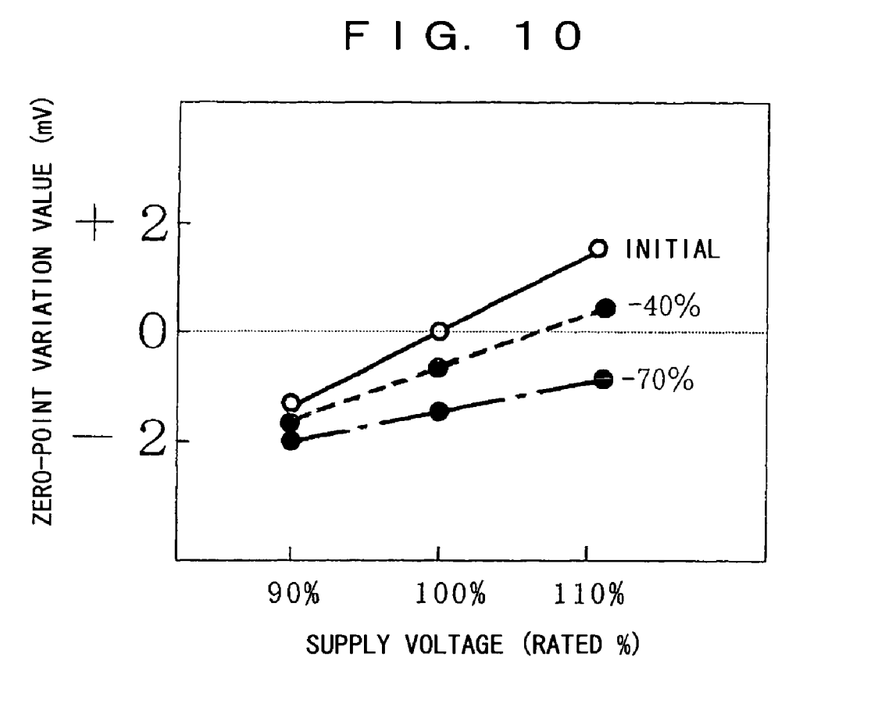
FIG. 10 is a diagram showing an example of the zero-point variation and deterioration in hydrogen sensitivity due to immersion of the sensor main body into ethyl acetate.
Figure 11:
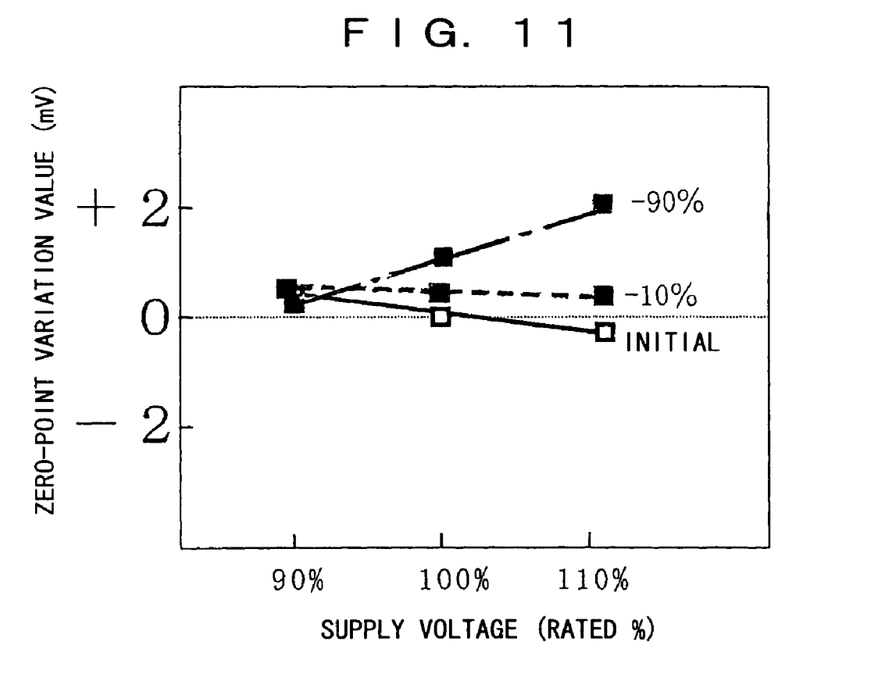
FIG. 11 is a diagram showing an example of the zero-point variation and deterioration in hydrogen sensitivity due to application of HMDS to the sensor main body.

FIG. 8 shows an example of the zero-point variation and the hydrogen sensitivity due to application of an impact to the sensor main body, and FIG. 9, FIG. 10, and FIG. 11 are diagrams each showing an example of the zero-point variation and deterioration in hydrogen sensitivity when the gas sensitivity of the sensor main body is deteriorated, FIG. 9 for immersion into 10% aqueous solution of sulfuric acid, FIG.

10 for immersion into ethyl acetate, and FIG. 11 for application of HMDS (hexamethyldisilazane).

Note that in the diagrams, a solid line shows an initial value, a broken line shows an experimental result when deterioration processing was performed once, and a one-dotted chain line shows an experimental result when deterioration processing was performed twice. On the right side of the broken line and the one-dotted chain line, percentages of deterioration from the initial sensitivity are indicated.

The example shown in FIG. 8 is an experimental example when a strong impact was given to the sensor main body, in which the zero-point variation occurred, but no deterioration in gas sensitivity occurred, resulting in little or no change in slope of the zero points with respect to the applied voltages.

In each of the experimental examples shown in FIG. 9 to FIG. 11, not only the zero point variation occurred but also the slope of the zero points with respect to the applied voltages significantly changed relative to the slope in the initial state. In particular, in the experimental example shown in FIG. 11, the slope of the zero points with respect to the applied voltages is inverted to the slope in the initial state (the slope is reverse) when the deterioration processing using HMDS was performed twice.

Hence, such properties can be used to realize the self-diagnosis function of the catalytic combustion type gas sensor.

For example, the voltage Vin applied from the power supply 5 to the gas sensing unit 10 shown in FIG. 4 and FIG. 5 is made changeable to any of three kinds of voltages 100%, any of 70% to 90%, and any of 110% to 130% relative to the rated voltage. Then, these voltages are applied in sequence to the gas sensing unit 10 in the clean atmosphere in the initial state (before factory shipment) so that the output voltages Vout (zero-point values) with respect to the applied voltages are measured, and the digital values obtained by converting the voltage values by the A-D conversion circuit 6 or the value of the slope of the zero points calculated therefrom is stored, as the initial value data, in an internal memory (for example, the ROM in the diagnostic microcomputer 7) of the gas sensor 1.

Further, when the gas sensor 1 is in an actual use (when the gas to be sensed does not exist), the diagnostic microcomputer 7 outputs a Vin control signal to the power supply 5 to cause the power supply 5 to apply in sequence the three kinds of voltages which are the same as those of the above-described voltages to the gas sensing unit 10, and the output voltages Vout (zero-point values) with respect to the applied voltages are measured. From the values, the value of the slope of the zero points is then calculated and compared with the initial value of the slope stored in the memory so that the presence or absence of abnormality such as deterioration in gas sensitivity or the like (hereinafter, referred only to as "abnormality") is determined (diagnosed). The presence or absence of abnormality is diagnosed, for example, by whether the change rate of the slope relative to the initial value exceeds the change rate of a diagnosis reference value which has been previously set.

Further, the case where the variation amount relative to the initial value of the zero point when the rated voltage is applied to the gas sensing unit 10 exceeds a preset range is also diagnosed as being abnormal.

The diagnostic result is sent to an equipment 8 with the gas sensor, so that when the diagnostic result is "normal," the gas sensor 1 is continuously used, whereas when the result is "abnormal," the operation is stopped or a warning informing of abnormality is issued on the equipment side.

The concrete self-diagnosis processing performed by the diagnostic microcomputer 7 of the gas sensor 1 shown in FIG. 5 will be described using the flowchart in FIG. 6. Prior to the description, the initial values and reference value for diagnosis which are stored in advance in the memory inside the sensor, for example, the ROM in the diagnostic microcomputer 7 or a memory such as a non-volatile memory separately provided or the like will be described.

In this embodiment, at the point in time of sensing the zero-point variation "corresponding to X % or greater of the initial value of the gas sensitivity," the diagnostic microcomputer 7 diagnoses the gas sensitivity as "abnormal (deteriorated)."

The "corresponding to X % or greater of the initial value of the gas sensitivity" here indicates that, for example, in a sensor with a hydrogen 4000 ppm sensitivity of 30 mV, the zero-point variation of 15 mV is X=50%. The value of X depends on the monitoring gas concentration in the equipment with the gas sensor and is a specification that the manufacturer of the equipment with the gas sensor sets and requests to the sensor manufacturer. Generally, it is considered that the value of X set to about 25% to about 50% is easy to handle in terms of safety. The diagnostic voltage value V0 (15 mV in the above-described example) corresponding to X is stored in the above-described memory in the manufacturing process of the sensor.

To diagnose the presence or absence of abnormality through use of the above-described change rate of slope of the zero points, an output voltage Vout(100) when the rated voltage is applied to the gas sensing unit 10, an output voltage Vout(90) when a 90%-voltage decreased by 10% from the rated voltage is applied, and an output voltage Vout(110) when a 110%-voltage increased by 10% from the rated voltage is applied, in the clean atmosphere in the initial state (before factory shipment) are measured and stored in the above-described memory as the initial values of the zero-point values. Alternatively, it is more preferable to store, in the above-described memory, as an initial value a0, the slope of the zero points calculated from the initial values of the zero points, that is, the value of the slope (calculated by, for example, the least square method) corresponding to the coefficient "a" of x in a straight line y=ax+b being a linear function as a result of plotting the output voltages (zero-point values) with respect to the applied voltages.

Since the change rate (Y) of the slope of the zero points relative to the initial value at the time of self-diagnosis corresponds to the deterioration rate (X) of the gas sensitivity, the change rate (Y) is calculated to diagnose the presence or absence of abnormality in this embodiment. For this reason, a permissible value Y0 of the change rate is also stored in the above-described memory. The value of Y0 is also set as a specification of the equipment with the gas sensor. The relation between the above-described change rate (Y) and the deterioration rate (X) is not unconditionally determined because it depends on the specifications of the gas sensor itself, the environment of the sensor attached to the equipment with the gas sensor, the cause of the deterioration in gas sensitivity, and so on. However, it is considered that setting of the relation to correspond to X=25% to 50% is desirable as described above.

The memory in the gas sensor 1 storing those kinds of data corresponds to an initial value storage means 11 in FIG. 1. When a diagnosis instruction signal is sent from the equipment 8 with the gas sensor to the gas sensor 1 during use of the gas sensor 1 installed in the equipment 8 with the gas sensor, the diagnostic microcomputer 7 executes the self-diagnosis processing shown in FIG. 6. Alternatively, a timer function of the diagnostic microcomputer 7 itself or a timer separately provided may be used to execute the self-diagnosis processing shown in FIG. 6 periodically at a time of day or time intervals preset in the memory.

Upon start of the self-diagnosis shown in the flowchart of FIG. 6, the diagnostic microcomputer 7 causes the power supply 5 to apply the voltage Vin(100) being 100% of the rated voltage to the gas sensing unit 10, and measures the output voltage of the gas sensing unit 10 at that time as the zero-point Vout(100) and stores it into the RAM.

Then, in step S2, the diagnostic microcomputer 7 determines whether or not the zero-point Vout(100) is equal to or greater than a negative value −V0 of the diagnostic voltage value V0 stored in the memory, and if no, the diagnostic microcomputer 7 diagnoses the gas sensor as abnormal and proceeds to step S11, in which it outputs an abnormal signal to the equipment 8 with the gas sensor and terminates the processing.

When determining that the zero-point Vout(100) is −V0 or greater in step S2, the diagnostic microcomputer 7 then determines in step S3 whether or not the zero-point Vout(100) is equal to or less than a positive value +V0 of the diagnostic voltage value V0, and if no, the diagnostic microcomputer 7 diagnoses the gas sensor as abnormal and proceeds to step S11, in which it outputs an abnormal signal to the equipment 8 with the gas sensor and terminates the processing.

In step S3, when the zero-point Vout(100) is equal to or less than +V0, the diagnostic microcomputer 7 proceeds to step S4, in which it causes the power supply 5 to apply the voltage Vin(90) being 90% of the rate voltage to the gas sensing unit 10, and measures the output voltage of the gas sensing unit 10 at that time as the zero-point Vout(90) and stores it into the RAM.

Subsequently, the diagnostic microcomputer 7 causes the power supply 5 to apply the voltage Vin(110) being 110% of the rate voltage to the gas sensing unit 10, and measures the output voltage of the gas sensing unit 10 at that time as the zero-point Vout(110) and stores it into the RAM.

Thereafter, in step S6, the diagnostic microcomputer 7 calculates a slope a1 of the zero points from the measurement results of the zero-points Vout(90), Vout(100), and Vout(110) with respect to the applied voltages obtained in steps S1, S4, and S5. The slope "a1" corresponding to the coefficient "a" of x in the straight line y=ax+b being a linear function as a result of plotting the output voltages (zero-point values) with respect to the applied voltages is calculated, for example, by the least square method similarly to the calculation of the slope of the above-described initial values.

In subsequent step S7, the diagnostic microcomputer 7 reads the initial value a0 of the slope of the zero points stored in the memory, or reads the values of the zero points with respect to the above-descried three kinds of voltages, if they are stored, and calculates the initial value a0 of the slope of the zero points similarly to the above.

In step S8, the diagnostic microcomputer 7 then calculates the change rate Y of the slope by an arithmetic operation of $Y=|\{(a1-a0)/a0\}|\times100$ (%) from the slope a1 of the zero points calculated from the measurement results and the initial value a0 of the slope of the zero points.

Subsequently, the diagnostic microcomputer 7 compares the change rate Y calculated in step S9 to the permissible value Y0 of the change rate stored in the memory, and if $Y\leqq Y0$, the diagnostic microcomputer 7 diagnoses the gas sensor as normal and then proceeds to step S10, in which the diagnostic microcomputer 7 outputs a normal signal to the equipment 8 with the gas sensor and terminates the processing. Alternatively, the diagnostic microcomputer 7 may perform nothing and terminate the processing as it is. Unless $Y\leqq Y0$ which means that the change rate Y exceeds the permissible value Y0, the diagnostic microcomputer 7 diagnoses the gas sensor as abnormal and proceeds to step S11, in which the diagnostic microcomputer 7 outputs an abnormal signal to the equipment 8 with the gas sensor and terminates the processing.

If the direction of the slope of the zero points at the time of self-diagnosis is reverse (inverted) to the slope of the initial zero points as in the case where the deterioration processing is performed twice with HMDS in FIG. 11, the signs of a0 and a1 are opposite, the absolute value of (a1−a0) is greater than a0. Accordingly, Y is equal to or greater than 100% so that $Y\leqq Y0$ is not established, the diagnostic microcomputer 7 will diagnose the gas sensor as abnormal. Note that the diagnostic microcomputer 7 may be configured such that it separately determine whether the directions of the slopes of a0 and a1 are the same or not (their plus or minus signs are the same or not), and if they are not the same, the diagnostic microcomputer 7 determines the gas sensor as abnormal.

If there occurs a malfunction such as deterioration or the like in the gas sensing unit 10, the gas sensor 1 according to this embodiment itself can diagnose the malfunction by the self-diagnosis function of the diagnostic microcomputer 7 and inform the equipment 8 with the gas sensor of the abnormality even without inspection using an actual gas. With the information, the equipment 8 with the gas sensor can stop its operation and issue a warning informing of the sensor abnormality (lighting or blinking of a warning lamp, generation of a warning sound by a buzzer, transmission of a signal informing a distal location of the sensor abnormality, and so on).

Consequently, it is possible to use continuously the gas sensor without anxiety until a warning is issued, and it is only required to replace the gas sensor with another immediately after the warning is issued. This can increase the reliability and safety of the equipment with the gas sensor as well as significantly reduce the cost required for its maintenance. The maintenance can be eliminated particularly for a household small equipment or system.

Note that the initial values and diagnostic reference values stored in the memory can be variously changed depending on the specifications, and the procedure of the self-diagnosis is not limited to the procedure of the above-described embodiment and variously changeable as long as it is in adherence with the spirit of the invention.

The catalytic combustion type gas sensor according to the invention is applicable in a wide range as equipment or system using various kinds of combustible gasses or a gas leakage sensing apparatus in a room having those apparatus and system installed. In particular, fuel cells which are desired to rapidly come into practical use needs to be equipped with a sensor for sensing leakage of hydrogen because the cells use combustible hydrogen gas as a fuel, and it is obligatory for a fuel-cell electric vehicle to have a hydrogen sensor installed for each section inside the fuel cell. Further, it is essential to provide a hydrogen gas sensor also in a fuel-cell system used as an industrial or household auxiliary power supply. It is very effective to apply the invention to those hydrogen sensors.

What is claimed is:

1. A catalytic combustion type gas sensor comprising a gas sensing unit having a first series circuit and a second series circuit connected in parallel to constitute a Wheatstone bridge circuit, said first series circuit having a sensing element and a compensation element connected in series, said sensing element having a heater coil embedded in a thermal conduction layer, said thermal conduction layer having an oxidation catalyst covering the surface thereof or carrying the catalyst, said oxidation catalyst causing a gas to be sensed to combust by contact, said compensation element having a heater coil with the same electric property as the heater coil of said sensing element embedded in a thermal conduction layer having no oxidation catalyst, and said second series circuit having a first resistor element and a second resistor element connected in series, in which a direct-current voltage is applied between connection points of said first series circuit and said second series circuit to output a voltage between a connection point of said sensing element and said compensation element and a connection point of said first resistor element and said second resistor element, as a detection signal, said gas sensor comprising:

a self-diagnosis unit for diagnosing a sensor abnormality wherein the self-diagnosis unit comprises:

an initial value storage means for storing the changes in voltage of the detection signal relative to the changes in the voltage value of the direct-current voltage to be applied between the connection points in the initial state or the slope thereof;

a measurement means for measuring the changes in voltage of the detection signal relative to the changes in the voltage value of the direct-current voltage to be applied between the connection points in the usage state;

a slope calculation means for calculating, from the changes in voltage of the detection signal measured by said measurement means, the slope thereof;

a change rate calculation means for calculating the change rate of the slope from the slope calculated by said slope calculation means and an initial value of the slope stored in said initial value storage means or an initial value of the slope calculated from the changes in voltage of the detection signal stored in said initial value storage means; and a diagnosis means for diagnosing the sensor abnormality when the change rate of the slope calculated by said change rate calculation means exceeds a reference value.

2. The catalytic combustion type gas sensor according to claim 1, wherein:

said initial value storage means is means for storing initial values of voltages of the detection signal when the direct-current voltage to be applied between the connection points in the initial state is switched among a rated voltage and voltages increased and decreased by predetermined percentages from the rated voltage, or of the slope of the zero points calculated from the voltages;

said measurement means is means for automatically switching the direct-current voltage to be applied between the connection points to each voltage among the rated voltage and the voltages increased and decreased by the predetermined percentages from the rated voltage in the usage state to measure the voltages of the detection signal when the each voltage is applied;

said slope calculation means is means for calculating the slope of the zero points from the voltage values measured by said measurement means; and said change rate calculation means is means for calculating the change rate of the slope from the slope of the zero points calculated by said calculation means and the initial value of the slope of the zero points stored in said initial value storage means or the initial value of the slope of the zero points calculated from the stored voltages of the detection signal.

3. The catalytic combustion type gas sensor according to claim 1, wherein said self-diagnosis unit has a function of starting a self-diagnosis operation for a sensor abnormality in accordance with an instruction from an equipment having said sensor attached thereto.

4. The catalytic combustion type gas sensor according to claim 1, wherein said self-diagnosis unit has a function of starting a self-diagnosis operation for a sensor abnormality in accordance with an instruction from an equipment having said sensor attached thereto.

5. The catalytic combustion type gas sensor according to claim 2, wherein said self-diagnosis unit has a function of starting a self-diagnosis operation for a sensor abnormality in accordance with an instruction from an equipment having said sensor attached thereto.

6. The catalytic combustion type gas sensor according to claim 1, wherein said self-diagnosis unit has a function of starting a self-diagnosis operation for a sensor abnormality periodically at preset time intervals.

7. The catalytic combustion type gas sensor according to claim 1, wherein said self-diagnosis unit has a function of starting a self-diagnosis operation for a sensor abnormality periodically at preset time intervals.

8. The catalytic combustion type gas sensor according to claim 2, wherein said self-diagnosis unit has a function of starting a self-diagnosis operation for a sensor abnormality periodically at preset time intervals.

9. The catalytic combustion type gas sensor according to claim 1, wherein the gas to be sensed is a hydrogen gas.

* * * * *